United States Patent [19]

Behre et al.

[11] Patent Number: 5,574,188

[45] Date of Patent: Nov. 12, 1996

[54] PROCESS FOR THE PREPARATION OF 4,6-DIAMINORESORCINOL

[75] Inventors: Horst Behre, Odenthal; Helmut Fiege, Leverkusen; Heinz-Ulrich Blank, Odenthal; Uwe Heinz; Wolfgang Eymann, both of Köln, all of Germany

[73] Assignee: Bayer Aktiengesellschaft, Leverkusen, Germany

[21] Appl. No.: 549,241

[22] Filed: Oct. 27, 1995

[30] Foreign Application Priority Data

Nov. 3, 1994 [DE] Germany ............ 44 39 191.9
Nov. 3, 1994 [DE] Germany ............ 44 39 185.4
Nov. 3, 1994 [DE] Germany ............ 44 39 194.3

[51] Int. Cl.⁶ ............................................. C07C 213/00
[52] U.S. Cl. ................... 564/418; 564/419; 564/423; 568/586; 568/933
[58] Field of Search ...................... 564/418, 419, 564/423

[56] References Cited

U.S. PATENT DOCUMENTS

| H726 | 1/1990 | Brown et al. | 564/428 |
| 4,766,244 | 8/1968 | Lysenko | 564/418 |
| 5,072,053 | 12/1991 | Blank et al. | 568/586 |
| 5,414,130 | 5/1995 | Lysenko et al. | 564/418 |

FOREIGN PATENT DOCUMENTS 0312931  4/1989  European Pat. Off. .
0402688  12/1990  European Pat. Off. .

OTHER PUBLICATIONS

E. Miller et al, "Methoden der Organischen Chemie" vol. IV/1C, p. 509, Georg Thieme Verlag, New York (1980).
Patent Abstract of Japan,, vol. 950, No. LX, Abstract of JP 07–648,321 (1995).

*Primary Examiner*—Richard L. Raymond
*Attorney, Agent, or Firm*—Sprung Horn Kramer & Woods

[57] ABSTRACT

4,6-diaminoresorcinol can be prepared in a plurality of steps in such a way that a) 1,3-dichlorobenzene is nitrated with a mixed acid of $HNO_3$, $H_2SO_4$ and $SO_3$ at 0 to 40° C. in anhydrous $H_2SO_4$, b) the resulting 1,3-dichloro-4,6/2,4-dinitrobenzene isomeric mixture is first reacted with benzyl alcohol in the presence of a strong base at −15° C. to +15° C. and then at 20° to 40° C. to give the dibenzyloxy compound and c) the 1,3-dibenzyloxy-4,6-dinitrobenzene isomer arising in pure form in b) is converted to the 4,6-diaminoresorcinol by catalytic hydrogenation.

17 Claims, No Drawings

PROCESS FOR THE PREPARATION OF 4,6-DIAMINORESORCINOL

BACKGROUND OF THE INVENTION

1. Field of the Invention

The present invention relates to a process for the preparation of 4,6-diaminoresorcinol from 1,3-dichlorobenzene by dinitration to give a 1,3-dichloro-4,6/2,4-dinitrobenzene mixture, subsequent reaction with sodium benzylate to give 1,3-dibenzyloxy- 4,6-dinitrobenzene and catalytic hydrogenation.

4,6-diaminoresorcinol is an important monomer building block for plastics, in particular polybenzoxazoles (macromolecules 1981, 915).

2. Description of the Related Art

In EP 0 402 688, the synthesis of 4,6-diaminoresorcinol from 1,3-dichloro-4,6-dinitrobenzene by reaction with sodium benzylate to give 1,3-dibenzyloxy-4,6-dinitrobenzene and subsequent catalytic hydrogenation is described. It is a disadvantage of the described process that pure 1,3-dichloro-4,6-dinitrobenzene is required for the synthesis which, after dinitration of 1,3-dichlorobenzene to give the 4,6/2,4-dinitro isomeric mixture, can only be obtained by a yield-reducing redissolution, e.g. from ethanol. Repetition of Examples 1 and 2 from EP 0 402 688 has also shown that the reaction of pure 1,3-dichloro-4,6-dinitrobenzene with sodium benzylate in benzyl alcohol at 50 or 55° C leads to considerable formation of benzaldehyde in an unknown side reaction which decreases the yield and quality in the formation of 1,3-dibenzyloxy-4,6-dinitrobenzene. A further disadvantage is the described embodiment of the heterogeneous catalytic hydrogenation of 1,3-dibenzyloxy-4,6-dinitrobenzene on the Pd/activated carbon catalyst as batch hydrogenation with subsequent aqueous hydrochloric acid work up of the hydrogenation batches which does not permit any economical recycling of the expensive noble metal catalyst.

SUMMARY OF THE INVENTION

It has now been found that 4,6-diaminoresorcinol can be prepared from 1,3-dichloro- 4,6-dinitrobenzene by reaction with sodium benzylate in benzyl alcohol to give 1,3-dibenzyloxy-4,6-dinitrobenzene and catalytic hydrogenation of 1,3-dibenzyloxy- 4,6-dinitrobenzene on the noble metal catalyst, if pure 1,3-dibenzyloxy- 4,6-dinitrobenzene is produced directly from 1,3-dichloro-4,6/2,4-dinitrobenzene isomeric mixtures, as are obtained, for example, by dinitration of 1,3-dichlorobenzene, by stepwise, temperature-stepped substitution of the chlorine atoms by the benzyloxy group under mild conditions with substantial avoidance of the undesirable side reaction to give benzaldehyde and the 1,3-dibenzyloxy-4,6-dinitrobenzene is reacted on the noble metal catalyst in an organic solvent at elevated pressure and elevated temperature by catalytic pumped hydrogenation to give 4,6-diaminoresorcinol.

The invention relates to a process for the preparation of 4,6-diaminoresorcinol from 1,3-dichlorobenzene by dinitration to give 1,3-dichloro-4,6-dinitrobenzene, by subsequent reaction with sodium benzylate in benzyl alcohol to give 1,3-dibenzyloxy- 4,6-dinitrobenzene and by subsequent catalytic hydrogenation of 1,3-dibenzyloxy- 4,6-dinitrobenzene on a noble metal catalyst which is characterized in that a) in a first step, 1,3-dichlorobenzene is reacted with a mixed acid containing nitric acid, sulphuric acid and 0.7 to 1.5 mol, preferably 0.8 to 1.2 mol, particularly preferably 0.9 to 1.1 mol, of $SO_3$ per mol of nitric acid in a temperature range from 0° to 40° C. in anhydrous sulphuric acid which contains 0 to 10 % by weight of free $SO_3$, the molar ratio of $HNO_3$ to 1,3-dichlorobenzene being 2 to 3, b) in a second step, the: 1,3-dichloro-4,6/2,4-dinitrobenzene isomeric mixtures obtained in a) which contain 0.1 to 60 % of 1,3-dichloro-2,4-dinitrobenzene, based on the total weight of the isomeric mixture, are reacted with 2 to 5 mol of benzyl alcohol and 2 to 5 equivalents of a strong base in the presence of an inert solvent, the process being carried out stepwise initially in the temperature range from −15° to +15° C. and then in the temperature range 20°–40° C. and c) in a third step the 1,3-dibenzyloxy-4,6-dinitrobenzene obtained in b) is converted to 4,6-diaminoresorcinol by catalytic pumped hydrogenation on a noble metal catalyst in an inert organic solvent at an $H_2$ pressure of 1 to 100 bar and a temperature of 20° to 100° C.

DETAILED DESCRIPTION OF THE INVENTION

To carry out the process according to the invention, it is essential in step a) that the nitration is carried out in anhydrous sulphuric acid, for example in 100% pure sulphuric acid or in sulphuric acid which contains 0 to 10% by weight of free $SO_3$. It is additionally essential that a mixed acid is used for the nitration which contains nitric acid, sulphuric acid and at least 0.7 mol of $SO_3$ per mol of nitric acid. Preferably, the mixed acid contains 0.8 to 1.2 mol of $SO_3$ per mol of nitric acid, particularly preferably 0.9 to 1.1 mol of $SO_3$. Such mixed acids can be prepared by mixing nitric acid and oleum. The proportion of sulphuric acid in the mixed acid can be chosen as desired; generally, it is 3 to 10 times that of 1,3dichlorobenzene (weight/weight).

Per mol of 1,3-dichlorobenzene, at least 2.0 mol of nitric acid, for example 2 to 3 mol of nitric acid, preferably 2.1 to 2.5 mol of nitric acid, particularly preferably 2.15 to 2.30 mol of nitric acid, are used in the form of mixed acid.

Step a) of the process according to the invention can be carried out in two different variants.

Variant 1:

1,3-dichlorobenzene is first added dropwise to a portion of anhydrous sulphuric acid or sulphuric acid which contains 0 to 10% by weight of free $SO_3$ and the mixed acid which contains nitric acid, sulphuric acid and at least 0.7 mol of $SO_3$ per mol of nitric acid is then added. The addition times for 1,3-dichlorobenzene are 5 minutes to 5 hours, for the mixed acid 15 minutes to 10 hours and are essentially a function of the reaction temperature and the efficiency of the refrigeration unit used and of the batch size. Preferred addition times for 1,3-dichlorobenzene are 15 to 60 minutes and for the mixed acid are 1 to 3 hours.

Variant 2:

1,3-dichlorobenzene and the mixed acid which contains nitric acid, sulphuric acid and at least 0.7 mol of $SO_3$ per mol of nitric acid are added simultaneously to a portion of anhydrous sulphuric acid or sulphuric acid which contains 0 to 10% by weight of free $SO_3$. In this preferred variant, the simultaneous addition time is 15 minutes to 10 hours, preferably 30 minutes to 3 hours, and is a function of the reaction temperature and the efficiency of the refrigeration unit used and of the batch size. In this preferred variant, in particular with the provision of sulphuric acid which contains 0 to 10% by weight of free SO3, the formation of 1,3dichlorobenzene sulphonic acids is virtually completely avoided.

The temperature of step a) of the process according to the invention is in the range from 0° to 40° C., preferably 10° to 30° C., in particular 15 to 25° C.

The nitration mixtures obtained by the process according to the invention are worked up in a manner known per se, for example by discharge into water or an ice/water mixture, filtration and water washing.

To carry out the process according to the invention it is essential in step b) that technical-grade 1,3-dichloro-4,6/2,4-dinitrobenzene isomeric mixtures obtained in step a) are reacted with at least two mol of benzyl alcohol and at least two equivalents of a strong base if appropriate in the presence of an inert solvent. These isomeric mixtures generally contain 0.1 to 60% of 1,3-dichloro-2,4-dinitrobenzene, based on the total weight of the mixture. Preferably, mixtures containing 5 to 25% of 1,3-dichloro-2,4-dinitrobenzene are used. Very particular preference is given to a mixture of 8 to 15% of 1,3-dichloro-2,4-dinitrobenzene and 85 to 92% of 1,3-dichloro-4,6-dinitrobenzene.

The 1,3-dichloro-4,6/2,4-dinitrobenzene isomeric mixture is reacted with 2 to 5 mol, preferably with 2 to 3 mol, of benzyl alcohol and with 2 to 5 equivalents of a strong base. The strong bases used are one or more selected from the group consisting of the alkali metals, such as lithium, sodium, potassium, rubidium or caesium, preferably sodium or potassium, the alkaline earth metals, such as magnesium, calcium, strontium or barium, preferably magnesium or calcium, the alkali metal hydroxides, such as lithium hydroxide, sodium hydroxide, potassium hydroxide, rubidium hydroxide, caesium hydroxide, preferably sodium hydroxide or potassium hydroxide, the alkaline earth metal hydroxides, such as magnesium hydroxide, calcium hydroxide, strontium hydroxide or barium hydroxide, preferably magnesium hydroxide or calcium hydroxide, the alkali metal carbonates, such as lithium carbonate, sodium carbonate, potassium carbonate, rubidium carbonate or caesium carbonate, preferably sodium carbonate or potassium carbonate, and the alkaline earth metal carbonates, such as magnesium carbonate, calcium carbonate, strontium carbonate or barium carbonate, preferably magnesium carbonate or calcium carbonate. Preferably, a strong base is used selected from the group consisting of the alkali metals, the alkali metal hydroxides and alkali metal carbonates, particularly preferably selected from the group consisting of sodium metal, sodium hydroxide and sodium carbonate. Likewise, the benzyl alcohol can also be used directly in the form of its alcoholate.

The temperature-stepped reaction is carried out in the first step in the temperature range from −15° C. to +15° C., preferably 0° to 15° C., in particular 5° to 15° C. and in the second reaction step in a temperature range from 20° to 40° C., preferably 25° to 35° C.

The inert solvent of which use is made is an aliphatic, aromatic or alkylaromatic hydrocarbon, a halogenated aromatic hydrocarbon or additional benzyl alcohol beyond the said 2 to 5 mol. Examples of such solvents are: pentane, hexane, heptane, octane, decane, dodecane and higher straight-chain or branched aliphatic hydrocarbons and mixtures thereof, such as ligroin or petroleum ether, benzene, toluene, ethylbenzene, chlorobenzene, bromobenzene, dichlorobenzene, dibromobenzene, chlorotoluene, dichlorotoluene or cyclohexane. Obviously, mixtures of a plurality of the said solvents can also be used.

In a preferred embodiment, benzyl alcohol is simultaneously used as reaction partner and solvent. In this case, benzyl alcohol is used in an amount of 3 to 20 parts by weight, preferably 5 to 15 parts by weight, based on 1 part by weight of dichloro-dinitrobenzene. Obviously, the benzyl alcohol can also be used in a mixture with the said inert solvents.

The reaction is independent of reaction pressure and is therefore expediently carried out at atmospheric pressure. An elevated pressure could be expedient if a low-boiling solvent is used. In this case, the inherent pressure automatically establishing itself is preferably employed. A reduced pressure is expedient if the temperature-stepped reaction is to be carried out under reflux at a constant boiling temperature in the first and/or second step.

The temperature-stepped reaction according to the invention of dichlorodinitrobenzene with benzyl alcohol in the presence of said bases generally requires reaction times of 15 minutes to 3 hours in the first step at a reaction temperature of 5° to 15° C., and generally requires reaction times of 30 minutes to 6 hours in the second step at a reaction temperature of 25° to 35° C. and gives high yields which exceed 90%.

The reaction product is sparingly soluble in the reaction medium and can therefore be isolated by simple filtration. The inorganic by-products (for example alkali metal chlorides and/or alkaline earth metal chlorides) can then be removed by slurrying in water and filtration once again.

To carry out the process according to the invention in step c), it is essential that 1,3-dibenzyloxy-4,6-dinitrobenzene is converted to 4,6-diaminoresorcinol by a catalytic pumped hydrogenation on the noble metal catalyst at elevated pressure and elevated temperature in an organic solvent. In this embodiment, a solution or suspension of 1,3-dibenzyloxy-4,6-dinitrobenzene in the organic solvent is pumped under hydrogenation conditions into a hydrogenation autoclave in which a suspension of the noble metal catalyst in the organic solvent or a solution of 4,6-diaminoresorcinol in the organic solvent under $H_2$ pressure has been placed.

In the catalytic hydrogenation of 1,3-dibenzyloxy-4,6-dinitrobenzene to 4,6-diaminoresorcinol, a simultaneous reduction of the nitro groups to the amino groups proceeds and the benzyl groups are eliminated, forming hydroxyl groups and toluene. The catalysts used are platinum group metals, such as palladium, platinum, rhodium or ruthenium, preferably palladium or platinum, on a suitable support. Suitable supports are activated carbon, $SiO_2$, $Al_2O_3$ and others. Highly particularly preferably, a palladium/activated carbon catalyst is used. The platinum group metal/support catalyst is used in an amount of 0.1 to 10% by weight of the platinum group metal, preferably 0.2 to 2% by weight, based on the weight of 1,3-dibenzyloxy-4,6-dinitrobenzene. The hydrogenation is carried out at an $H_2$ pressure of 1 to 100 bar, preferably 5 to 50 bar, in particular 10 to 30 bar and in the temperature range from 20° to 100° C., preferably 40° to 80° C.

The liquid reaction medium used for the hydrogenation can be an alcohol, an ether, an aromatic or alkyl aromatic hydrocarbon, an organic acid or a mixture of a plurality thereof. Examples of such liquid reaction media are methanol, ethanol, propanol, isopropyl alcohol, butanol, isobutanol, tetrahydrofuran, dioxane, benzene, toluene, xylene, dimethoxy-ethane, diethoxy-ethane, 1,2-dimethoxypropane and other glycol mono- and diethers, acetic acid, propionic acid or a mixture of a plurality thereof. In the case of water-soluble liquid reaction media, the organic part of this reaction medium can be replaced by water up to an extent of 75% by weight. However, it is essential that the liquid reaction medium, at the hydrogenation temperature, has sufficient dissolving capacity for the 4,6-diaminoresorcinol formed, in order to ensure simple separation and recycling of the platinum group metal/support catalyst, for example by forcing out and filtering the dissolved 4,6-diaminoresorcinol from the hydrogenation autoclave, for instance using nitrogen via a riser pipe which is furnished with a sintered metal frit. Methanol is preferably used as liquid reaction medium. The entire liquid reaction medium for the hydrogenation is used in an amount of 2 to 50 parts by weight, preferably 5 to 25 parts by weight, based on 1 part by weight to 1,3-dibenzyloxy- 4,6-dinitrobenzene.

In detail, the process according to the invention is carried out as follows: 1,3-dichlorobenzene and mixed acid (equimolar mixture of $HNO_3$ and $SO_3$ as oleum 65) are added simultaneously to a portion of sulphuric acid monohydrate at 20° C. in the course of approximately of 1 h with cooling, where the molar ratio of $HNO_3$ to 1,3-dichlorobenzene is to be for example about 2.2:1. The nitration mixture is further stirred for approximately 4 h at 20° C., discharged into an ice/water mixture up to a maximum temperature of 20° C. and the resulting aqueous suspension is further stirred for 1 h at 20° C. The product which is very easy to filter is isolated, washed acid-free with water and if appropriate dried (technical-grade 4,6/2,4-dinitro-1,3-dichlorobenzene mixture).

The technical-grade 4,6/2,4-dinitro-1,3-dichlorobenzene mixture obtained (90:10) is introduced into a freshly prepared solution of sodium benzylate in benzyl alcohol at about 10° C. under nitrogen in the course of approximately ½ h with cooling, where the molar ratio of 4,6/2,4-dinitro-1,3-dichlorobenzene mixture to sodium benzylate is to be, for example, about 1:2.4. The resulting suspension of principally 1-benzyloxy-3-chloro-4,6/2,4-dinitrobenzene mixture is further stirred for approximately ½ h at 10° C., heated to 30° C. and further stirred for approximately 3 h at 30° C. until complete conversion into the mixture of dibenzyloxy compounds. The 1,3-dibenzyloxy-4,6-dinitrobenzene in the mixture precipitating out with NaCl, and which is very easy to filter, is isolated at 30° C. via a glass sinter suction filter and the liquid is pressed off thoroughly. To separate off NaCl and adhering benzyl alcohol, the product is slurried in approximately five times the amount of water, stirred for 1 h at room temperature (20° C.) filtered once again and washed with water.

In a hydrogenation autoclave, a suspension of Pd(5%)/ activated carbon catalyst in methanol is introduced. Under hydrogenation conditions (60° C.; 20 bar $H_2$) a 5– 10% strength by weight suspension of 1,3-dibenzyloxy-4,6-dinitrobenzene in methanol is pumped in the course of 30–90 minutes, where the concentration of 1,3-dibenzyloxy-4,6-dinitrobenzene, based on the total amount of methanol, is to be 5 to 7.5% by weight and the weight ratio of 1,3-dibenzyloxy-4,6dinitrobenzene to palladium is to be approximately 85:1. After hydrogenation absorption has been completed, the reaction mixture is further stirred for approximately 60 minutes at 60° C. and 20 bar $H_2$, the stirrer is stopped and approximately 75% of the methanolic 4,6-diaminoresorcinol solution is forced out of the hydrogenation autoclave, for example using nitrogen via a riser tube which is furnished with a sintered metal frit, into a receiver into aqueous hydrochloric acid. After distilling off the organic solvent, the 4,6-diaminoresorcinol can be isolated as stable dihydrochloride by evaporating the resulting aqueous hydrochloric acid solution and, if appropriate, can be purified by redissolving. In the same manner, numerous hydrogenations can be carried out one after the other without decreasing catalyst activity with the Pd(5%)/activated carbon catalyst used, which leads to a very low catalyst consumption.

It is considered to be decidedly surprising that, under the conditions according to the invention in step a) it is possible to prepare successfully 1,3-dichloro-4,6-dinitrobenzene in a non-hazardous manner in improved yield and quality (see comparison examples). When the mixed acid according to the invention is used, the dinitration of 1,3-dichlorobenzene can be carried out at considerably lower temperatures in comparison with the prior art, which avoids the formation of higher-nitrated, shock-sensitive products. Moreover, because the substantially lower content of the isomeric 1,3-dichloro-2,4-dinitrobenzene, a yield-reducing product purification by redissolution in ethanol can be dispensed with.

It is further considered surprising that by the process according to the invention in step b), in the preferred embodiment using benzyl alcohol simultaneously as reaction partner and solvent, 1,3-dibenzyloxy-4,6-dinitrobenzene is obtained in pure form even when 1,3-dichloro-4,6/ 2,4-dinitrobenzene isomeric mixtures are used in the reaction which contain up to 60% of 1,3-dichloro-2,4-dinitrobenzene, based on the total weight of the mixture. The isomeric 1,3-dibenzyloxy-2,4dinitrobenzene present as the main product in such a case remains completely in solution. Moreover, by the process according to the invention, due to the temperature-stepped reaction, in comparison with the prior art, significantly less benzaldehyde is formed from benzyl alcohol in an unknown side reaction.

For step c) of the process according to the invention it is considered surprising that numerous hydrogenations can be carried out one after the other by catalytic pumped hydrogenation without decrease of the catalyst activity, although it is known that the resulting amines, as do amines in general, inhibit platinum group metal catalysts in the course of the reaction, so that an addition of acid is recommended to bind the resulting amines. (Houben-Weyl, Handbuch der organischen Chemie, [Handbook of Organic Chemistry], Volume 4; 1 c. p. 509 (1980)).

The process according to the invention can be carried out discontinuously and continuously.

EXAMPLES

Example 1 (Technical-grade 1,3-dichloro-4,6/2,4-dinitrobenzene mixture)

700 g of sulphuric acid monohydrate (7.14 mol) were placed in a multineck flask-stirrer set-up having an internal thermometer and two metering dropping funnels for 1,3-dichlorobenzene and mixed acid. 147 g of 1,3-dichlorbenzene 99.4% pure (0.99 mol) and 506 g of mixed acid (2.20 mol of $HNO_3$) were added simultaneously in the course of 1 h at 20° C. with stirring and ice cooling, where crystallization of the nitration product began after approximately 30 min. The reaction mixture was further stirred for 4 h at 20° C. The reaction mixture was poured into a portion of 3640 g of ice/water mixture with stirring, up to a maximum temperature 20° C. in the course of approximately 30 min. The resulting product suspension was further stirred for 1 h at 20° C., the reaction product which was very easy to filter was isolated via a glass sinter suction filter and washed acid-free with a total of approximately 3750 g of water and dried at 40° C. in vacuo.

226 g of 1,3-dichloro-4,6-dinitrobenzene (dry) were obtained.

The content of the isolated product determined by GC was:
  89.7% by weight 1,3-dichloro-4,6-dinitrobenzene,
  10.1% by weight 1,3-dichloro-2,4-dinitrobenzene,
  0.1% by weight 1,3-dichloro-2-nitrobenzene,
  0.1% by weight 1,3-dichloro-4-nitrobenzene.

The yield of 1,3-dichloro-4,6-dinitrobenzene in the form of 4,6/2,4-dinitro mixture was 86.4% of the theoretical yield, based on 1,3-dichlorobenzene used.

The mixed acid was prepared as follows: 141.4 g=2.20 mol of HNO₃ 90% pure were taken. 365 g of oleum 65 (3.0 mol of SO₃; 1.3 mol of H₂SO₄) were added dropwise in the course of several hours with ice cooling and stirring up to a maximum temperature of 35° C.

Example 2 (Technical-grade 1,3-dichloro-4,6/2,4-dinitrobenzene mixture)

A reaction carried out as in Example 1, but in which 2.3 mol of HNO₃ is the form of the mixed acid used in Example 1 were added simultaneously with 1.0 mol of 1,3-dichlorobenzene to 600 g of sulphuric acid monohydrate at 10° C. in the course of 1.5 h, gave 228 g of 1,3-dichloro-4,6-dinitrobenzene (dry). The content of the isolated product determined by GC was:

89.8% by weight 1,3-dichloro-4,6-dinitrobenzene,
9.3% by weight 1,3-dichloro-2,4-dinitrobenzene,
0.2% by weight 1,3-dichloro-2-nitrobenzene,
0.7% by weight 1,3-dichloro-4-nitrobenzene.

The yield of 1,3-dichloro-4,6-dinitrobenzene in the form of the 4,6/2,4-dinitro mixture was 86.4% of the theoretical yield, based on 1,3-dichlorobenzene used.

Example 3 (Technical-grade 1,3-dichloro-4,6/2,4-dinitrobenzene mixture)

A reaction carried out as in Example 1, but in which 2.2 mol of HNO₃ in the form of the mixed acid used in Example 1 were added simultaneously with 1.0 mol of 1,3-dichlorobenzene to 700 g of sulphuric acid monohydrate at 40° C. in the course of 2 h, gave 220 g of 1,3-dichloro-4,6-dinitrobenzene (dry). The content of the isolated product determined by GC was:

87.6% by weight 1,3-dichloro-4,6-dinitrobenzene,
11.5% by weight 1,3-dichloro-2,4-dinitrobenzene,
0.2% by weight 1,3-dichloro-2-nitrobenzene,
0.7% by weight 1,3-dichloro-4-nitrobenzene.

The yield of 1,3-dichloro-4,6-dinitrobenzene in the form of the 4,6/2,4-dinitro mixture was 81.3% of the theoretical yield, based on 1,3-dichlorobenzene used.

Example 4 (Technical-grade 1,3-dichloro-4,6/2,4-dinitrobenzene mixture; comparison example, not according to the invention)

795 g of sulphuric acid monohydrate (8.1 mol) were placed in a set-up as described in Example 1. 259 g of 1,3-dichlorobenzene 99.4% pure (1.75 mol) were added dropwise in the course of approximately 45 min with stirring. 740 g of mixed acid not according to the invention (67% of H₂SO₄, 33% of HNO₃, in total 3.88 mol of HNO₃) were then added in the course of approximately 4 h, 55° C. being achieved after approximately 40 min. The temperature as maintained in the further course of the reaction. The reaction mixture was further stirred for 4 h at 55° C. The reaction mixture was poured into a portion of 4000 g ice/water mixture in the course of approximately 30 min with stirring up to a maximum temperature of 20° C. The resulting product suspension was further stirred for 1 h at 20° C., the reaction product was isolated via a glass sinter suction filter, washed acid-free with water and dried at 40° C. in vacuo.

374 g of 1,3-dichloro-4,6-dinitrobenzene (dry) were obtained.

The content of the isolated product determined by GC was:

85.4% by weight 1,3-dichloro-4,6-dinitrobenzene,
14.3% by weight 1,3-dichloro-2,4-dinitrobenzene,
0.1% by weight 1,3-dichloro-2-nitrobenzene,
0.2% by weight 1,3-dichloro-4-nitrobenzene.

The yield of 1,3-dichloro-4,6-dinitrobenzene in the form of the 4,6/2,4-dinitro mixture was 76.6% of the theoretical yield, based on 1,3-dichlorobenzene used.

Example 5 (Technical-grade 1,3-dichloro-4,6/2,4-dinitrobenzene mixture; comparison example, not according to the invention)

336 g of mixed acid not according to the invention (67% of H₂SO₄, 33% of HNO₃; in total 1.76 mol of HNO₃) were placed in a set up as described in Example 1.64 g of 1,3-dichlorobenzene 99.4% pure (0.44 mol) were added dropwise in the course of 1 h at 5° to 15° C. with stirring and cooling. After the cooling bath was removed, the exothermic reaction led to a marked temperature increase. The reaction mixture was further stirred for 2 h at 80° C. The reaction mixture was poured into a portion of 1800 g of ice/water mixture with stirring up to a maximum temperature of 20° C. in the course of approximately 30 min. The resulting product suspension was stirred for a further 1 h at 20° C., the reaction product was isolated via a glass sinter suction filter, washed acid-free with water and dried at 40° C. in vacuo.

91 g of 1,3-dichloro-4,5-dinitrobenzene (dry) were obtained.

The content of the isolated product determined by GC was:

84.0% by weight 1,3-dichloro-4,6-dinitrobenzene,
14.3% by weight 1,3-dichloro-2,4-dinitrobenzene,
1.7% by weight of unknown compounds.

The yield of 1,3-dichloro-4,6-dinitrobenzene in the form of the 4,6/2,4-dinitro mixture was 73.2% of the theoretical yield, based on 1,3-dichlorobenzene used.

Example 6 (1,3-benzyloxy-4,6-dinitrobenzene)

1560 g of benzyl alcohol were placed in a multinecked flask-stirrer set-up having an internal thermometer and an entry for solids. 74 g of ground NaOH (1.85 mol) were introduced in the course of approximately of 15 min, passing through dry nitrogen and with ice cooling, up to a maximum temperature of 25° C. The reaction mixture was further stirred up to complete dissolution for approximately 12 h at room temperature (20° C.). 183 g of 1,3-dichloro-4,6/2,4-dinitrobenzene isomer mixture (0.685 mol of 1,3-dichloro-4,6-dinitrobenzene, 0.085 mol of 1,3-dichloro- 2,4-dinitrobenzene) were introduced into the yellowish, slightly hazy reaction solution in the course of approximately 30 min at 10° C., passing through dry nitrogen and with ice/NaCl cooling. The resulting light-yellow suspension was further stirred for 30 min at 10° C., then heated to 30° C. and further stirred for approximately 3 h at this temperature. The precipitated product mixture, which was very easy to filter, of 1,3-dibenzyloxy-4,6-dinitrobenzene and NaCl was isolated at 30° C. via a glass sinter suction filter and sucked thoroughly dry to remove the benzyl alcohol mother liquor. The isolated crude product was poured into a portion of 2500 g of water with stirring at 20° C., the resulting suspension was stirred up to complete dissolution of NaCl for approximately 1 h at 20° C., the purified, virtually colourless product was filtered once again, washed with approximately 5000 g of water in a plurality of portions up to complete removal of benzyl alcohol, and dried in vacuo at 60° C.

237 g of pure product (dry) were obtained.

The content of the isolated product determined by high pressure liquid chromatography (HPLC) was:

| | |
|---|---|
| Content (titanium reduction), molecular weight 380 | 99.8% by weight, of which (by HPLC), |
| 1,3-dibenzyloxy-4,6-dinitrobenzene | 99.1% by weight, |
| 1-benzyloxy-3-chloro-4,6-dinitrobenzene | 0.6% by weight, |
| 1,3-dibenzyloxy-2,4-dinitrobenzene | <0.1% by weight, |
| unknown compounds | 0.2% by weight. |

The yield of 1,3-dibenzyloxy-4,6-dinitrobenzene was 91.0% of the theoretical yield, based on 1,3-dichloro-4,6-dinitrobenzene used in the form of the 1,3-dichloro- 4,6/2,4-dinitrobenzene mixture. The benzaldehyde content in the benzyl alcohol mother liquor was 0.5% by GC.

Example 7 (1,3-dibenzyloxy-4,6-dinitrobenzene)

A reaction carried out as in Example 6, but in which a mixture of 1000 ml of benzyl alcohol and 500 ml of toluene was used, gave 236 g of pure product (dry).

The content of the isolated product determined by HPLC was:

| | |
|---|---|
| Content (titanium reduction), molecular weight 380 | 99.8% by weight, of which (by HPLC), |
| 1,3-dibenzyloxy-4,6-dinitrobenzene | 98.8% by weight, |
| 1-benzyloxy-3-chloro-4,6-dinitrobenzene | 0.6% by weight, |
| 1,3-dibenzyloxy-2,4-dinitrobenzene | <0.1% by weight, |
| unknown compounds | 0.5% by weight. |

The yield of 1,3-dibenzyloxy-4,6-dinitrobenzene was 90.5% of the theoretical yield, based on 1,3-dichloro-4,6-dinitrobenzene used in the form of the 1,3-dichloro- 4,6/2,4-dinitrobenzene mixture. The benzaldehyde content in the benzyl alcohol mother liquor was 0.6% by GC.

Example 8 (1,3-dibenzyloxy-4,6-dinitrobenzene)

A reaction carried out as in Example 6, but in which pure 1,3-dichloro-4,6-dinitrobenzene (0.77 mol) was used, gave 271 g of pure product (dry).

The content of isolated product determined by HPLC was:

| | |
|---|---|
| Content (titanium reduction), molecular weight 380 | 99.9% by weight, of which (by HPLC), |
| 1,3-dibenzyloxy-4,6-dinitrobenzene | 99.1% by weight, |
| 1-benzyloxy-3-chloro-4,6-dinitrobenzene | 0.8% by weight, |
| unknown compounds | 0.1% by weight. |

The yield of 1,3-dibenzyloxy-4,6-dinitrobenzene was 92.5% of the theoretical yield, based on 1,3-dichloro-4,6-dinitrobenzene used. The benzaldehyde content in the benzyl alcohol mother liquor was 0.3% by GC.

Example 9 (1,3-dibenzyloxy-4,6-dinitrobenzene)

A reaction carried out as in Example 6, but in which a 1,3-dichloro-4,6/2,4-dinitrobenzene mixture (0.77 mol) containing 59% of 1,3-dichloro-2,4-dinitrobenzene was used, gave 99 g of pure product (dry).

The content of the isolated product determined by HPLC was:

| | |
|---|---|
| Content (titanium reduction), molecular weight 380 | 99.9% by weight, of which (by HPLC), |
| 1,3-dibenzyloxy-4,6-dinitrobenzene | 97.5% by weight, |
| 1-benzyloxy-3-chloro-4,6-dinitrobenzene | 1.4% by weight, |
| 1,3-dibenzyloxy-2,4-dinitrobenzene | 0.9% by weight, |
| unknown compounds | 0.2% by weight. |

The yield of 1,3-dibenzyloxy-4,6-dinitrobenzene was 82.0% of the theoretical yield, based on 1,3-dichloro-4,6-dinitrobenzene used. The benzaldehyde content in the benzyl alcohol mother liquor was 0.7% by GC.

Example 10 (1,3-dibenzyloxy-4,6-dinitrobenzene; comparison example, not according to the invention)

A reaction carried out as in Example 6, but in which pure 1,3-dichloro-4,6-dinitrobenzene (0.77 mol) was poured into the sodium benzylate/benzyl alcohol solution up to a temperature of 50° C. and the reaction mixture was further stirred for 30 min at 50° C., gave 262 g of a brownish product (dry).

The content of the isolated product determined by HPLC was:

| | |
|---|---|
| Content (titanium reduction), molecular weight 380 | 98.9% by weight, of which (by HPLC), |
| 1,3-dibenzyloxy-4,6-dinitrobenzene | 97.8% by weight, |
| 1-benzyloxy-3-chloro-4,6-dinitrobenzene | 0.4% by weight, |
| unknown compounds | 1.8% by weight. |

The yield of 1,3-dibenzyloxy-4,6-dinitrobenzene was 88.5% of the theoretical yield, based on 1,3-dichloro-4,6-dinitrobenzene used. The benzaldehyde content in the benzyl alcohol mother liquor was 2.5% by GC.

Example 11 (4,5-diaminoresorcinol)

A suspension of 15 g of Pd (5%)/activated carbon catalyst (moist; 6 g dry; 0.3 g of Pd) in 160 g of methanol was placed in a 1.3 l hydrogenation autoclave. 480 g of a 5% strength by weight 1,3-dibenzyloxy-4,6-dinitrobenzene/methanol suspension (0.063 mol) were pumped in under hydrogenation conditions at 60° C. at 20 bar $H_2$ in the course of approximately 30 min. The reaction mixture was further stirred for approximately 3 h at 60° C. and 20 bar $H_2$ until hydrogen absorption was completed, the stirrer was stopped and approximately 75% of the methanolic 4,6-diaminoresorcinol solution was forced out of the hydrogenation autoclave by means of nitrogen via a riser tube which was furnished with a sintered metal frit into a portion of 120 g of 10% strength by weight aqueous hydrochloric acid. After distilling off the organic solvent, the 4,6-diaminoresorcinol formed was isolated as a stable dihydrochloride by evaporating the resulting aqueous hydrochloric acid solution. In the same manner, a further 480 g of the 5% strength by weight 1,3-dibenzyloxy-4,6-dinitrobenzene/methanol suspension were pumped at 60° C. and 20 bar $H_2$ in the course of approximately 30 min into the suspension remaining in the hydrogenation autoclave of the Pd (5%)/activated carbon catalyst in approximately 160 g of 4,6-diaminoresorcinol/methanol solution and hydrogenated without decrease of the catalyst activity. In this manner, a total of 5 hydrogenations were carried out one after the other with the catalyst reused four times.

In total, 64.1 g of 4,6-diaminoresorcinol dihydrochloride (dry) were obtained.

According to HPLC, the 1,3-dibenzyloxy-4,6-dinitrobenzene used was completely subverted and the 4,6-diaminoresorcinol dihydrochloride isolated was virtually uniform by chromatography. According to $^1$HNMR, the isolated products did not contain any benzyl groups.

| | |
|---|---|
| Content (from chlorine) molecular weight 213 | 97.3% by weight, |
| Content (from nitrogen) molecular weight 213 | 98.1% by weight. |

The yield of 4,6-diaminoresorcinol was 93.0% of the theoretical yield (from chlorine), based on 1,3-dibenzyloxy-4,6-dinitrobenzene used or 93.7% of the theoretical yield (from nitrogen), based on 1,3-dibenzyloxy-4,6-dinitrobenzene used.

Example 12 (4,6-diaminoresorcinol)

A reaction carried out as in Example 11, but in which 480 g of 7.5% strength by weight 1,3-dibenzyloxy-4,6-dinitrobenzene/methanol suspension (0.095 mol) were pumped in, gave 85.5 g of 4,6-diaminoresorcinol dihydrochloride (dry) after a total of five hydrogenations with reuse four times.

Content (from chlorine) molecular weight 213 97.0% by weight.

The yield of 4,6-diaminoresorcinol was 82.0% of the theoretical yield (from chlorine), based on 1,3-dibenzyloxy-4,6-dinitrobenzene.

Example 13. (4,6-diaminoresorcinol)

A reaction carried out as in Example 11, but in which a suspension of 24 g of Pd (5%)/activated carbon catalyst (moist; 8.9 g dry; 0.44 g of Pd) in 160 g of methanol was placed in the 1.3 l hydrogenation autoclave, gave 63.8 g of 4,6-diaminoresorcinol dihydrochloride (dry) after a total of five hydrogenations with reuse of the catalyst four times.

| Content (from chlorine) molecular weight 213 | 98.2% by weight |
|---|---|

The yield of 4,6-diaminoresorcinol was 93.4% of theoretical yield (from chlorine), based on 1,3-dibenzyloxy-4,6-dinitrobenzene used.

What is claimed is:

1. A process for the preparation of 4,6-diaminoresorcinol from 1,3-dichloro-benzene by dinitration to give 1,3-dichloro-4,6-dinitrobenzene, by subsequent reaction with sodium benzylate in benzyl alcohol to give 1,3-dibenzyloxy-4,6-dinitrobenzene and by subsequent catalytic hydrogenation of 1,3-dibenzyloxy-4,6-dinitrobenzene on a noble metal catalyst, wherein
   a) in a first step, 1,3-dichlorobenzene is reacted with a mixed acid containing nitric acid, sulphuric acid and 0.7 to 1.5 mol of $SO_3$ per mol of nitric acid in a temperature range from 0° to 40° C. in anhydrous sulphuric acid which contains 0 to 10% by weight of free $SO_3$, the molar ratio of $HNO_3$ to 1,3-dichlorobenzene being 2 to 3,
   b) in a second step, the 1,3-dichloro-4,6/2,4-dinitrobenzene isomeric mixtures obtained in a) which contains 0.1 to 50% of 1,3-dichloro-2,4-dinitrobenzene, based on the total weight of the isomeric mixture, are reacted with 2 to 5 mol of benzyl alcohol and 2 to 5 equivalents of a strong base in the presence of an inert solvent, the process being carried out stepwise initially in the temperature range from −15° to +15° C. and then in the temperature range 20°–40° C. and
   c) in a third step the 1,3-dibenzyloxy-4,6-dinitrobenzene obtained in b) is converted to 4,6-diaminoresorcinol by catalytic pumped hydrogenation on a noble metal catalyst in an inert organic solvent at an $H_2$ pressure of 1 to 100 bar and a temperature of 20° to 100° C.

2. The process of claim 1, wherein in step a) 0.8 to 1.2 mol of $SO_3$ per mol of nitric acid are used.

3. The process of claim 2, wherein in step a) 0.9 to 1.1 mol of $SO_3$ per mol of nitric acid are used.

4. The process of claim 1, wherein per mol of 1,3-dichlorobenzene 2.1 to 2.5 mol of nitric acid are used in the form of the mixed acid.

5. The process of claim 1, wherein per mol of 1,3-dichlorobenzene 2.15 to 2.30 mol of nitric acid are used in the form of the mixed acid.

6. The process of claim 1, wherein 1,3-dichlorobenzene and mixed acid are added simultaneously to a portion of anhydrous sulphuric acid.

7. The process of claim 1, wherein the strong bases used are one or more selected from the group consisting of the alkali metals, alkaline earth metals, alkali metal hydroxide, alkaline earth metal hydroxides, alkali metal carbonates and alkaline earth metal carbonates.

8. The process of claim 7, wherein the strong bases used are selected from the group consisting of the alkali metals, alkali metal hydroxides and alkali metal carbonates.

9. The process of claim 8, wherein the strong bases used are selected from the group consisting of sodium metal, sodium hydroxide and sodium carbonate.

10. The process of claim 1, wherein the inert solvent used is an aliphatic, aromatic or alkylaromatic hydrocarbon, a halogenated aromatic hydrocarbon or additional benzyl alcohol in an amount of 3 to 20 parts by weight based on 1 part by weight of dichloro-dinitrobenzene.

11. The process of claim 10, wherein the inert solvent used is additional benzyl alcohol.

12. The process of claim 10, wherein the inert solvent used is in an amount of 5 to 15 parts by weight based on 1 part by weight of dichloro-dinitrobenzene.

13. The process of claim 1, wherein a temperature-stepped reaction is carried out in the first step in a temperature range from 5° to 15° C. and in a second reaction step in a temperature range from 25° to 35° C.

14. The process of claim 1, wherein the liquid reaction medium used for the catalytic pumped hydrogenation is an alcohol, an ether, an aromatic or alkylaromatic hydrocarbon, an organic acid or a mixture of a plurality thereof in an amount of 2 to 50 parts by weight, based on 1 part by weight of 1,3-dibenzyloxy-4,6-dinitrobenzene.

15. The process of claim 14, wherein the liquid reaction medium is in an amount of 5 to 25 parts by weight, based on 1 part by weight of 1,3-dibenzyloxy- 4,6-dinitrobenzene.

16. The process of claim 14, wherein the liquid reaction medium used for the catalytic pumped hydrogenation is methanol, ethanol, propanol, isopropanol, butanol, isobutanol, tetrahydrofuran, dioxane, benzene, toluene, xylene, dimethoxy-ethane, diethoxy-ethane, 1,2-dimethoxypropane and other glycol mono- and diethers, acetic acid, propionic acid or a mixture of a plurality thereof, where in the case of a water-soluble reaction medium, this reaction medium can be replaced by water up to the extent of 75% by weight.

17. The process of claim 1, wherein the catalytic pumped hydrogenation is carried out in methanol on the palladium/ activated carbon catalyst in an amount of 0.2 to 2% by weight of the platinum group metal, based on the weight of 1,3-dibenzyloxy-4,6-dinitrobenzene, at an $H_2$ pressure of 10 to 30 bar and in the temperature range from 40° to 80° C., where methanol is used in an amount of 5 to 25 parts by weight, based on 1 part by weight of 1,3-dibenzyl oxy-4,6-dinitrobenzene.

* * * * *